United States Patent [19]

Markham

[11] Patent Number: 5,147,378
[45] Date of Patent: Sep. 15, 1992

[54] GRAPSING FORCEPS

[76] Inventor: Harold Markham, 508 N. Rexford Dr., Beverly Hills, Calif. 90210

[21] Appl. No.: 664,778

[22] Filed: Mar. 5, 1991

[51] Int. Cl.$^5$ .............................................. A61B 17/28
[52] U.S. Cl. ...................................... 606/206; 606/210
[58] Field of Search ................................ 606/205-208, 606/174, 170, 210, 140, 141; 128/751, 752

[56] References Cited

U.S. PATENT DOCUMENTS

| | | | |
|---|---|---|---|
| 3,404,677 | 10/1968 | Springer | 606/206 X |
| 3,820,544 | 6/1974 | Semm | 606/141 X |
| 4,427,014 | 1/1984 | Bel et al. | 606/206 X |
| 4,896,678 | 1/1990 | Ogawa | 606/170 X |
| 4,990,152 | 2/1991 | Yoon | 606/140 |

OTHER PUBLICATIONS

Preston et al "New Rectal-Mucosal Biopsy Forceps"- *The Lancet* Jan. 22, 1983 p. 157.

*Primary Examiner*—Michael H. Thaler
*Attorney, Agent, or Firm*—Poms, Smith, Lande & Rose

[57] ABSTRACT

Forceps for grasping tissue material comprising a stationary stylet telescopingly disposed within a cannula. Jaws are mounted to one end of the stylet and the other end of the stylet is fixedly mounted in a handle. The cannula is mounted to the handle for sliding movement over the jaws to selectively compress and release the same to grasp and release tissue material or the like engaged by the jaws.

3 Claims, 3 Drawing Sheets

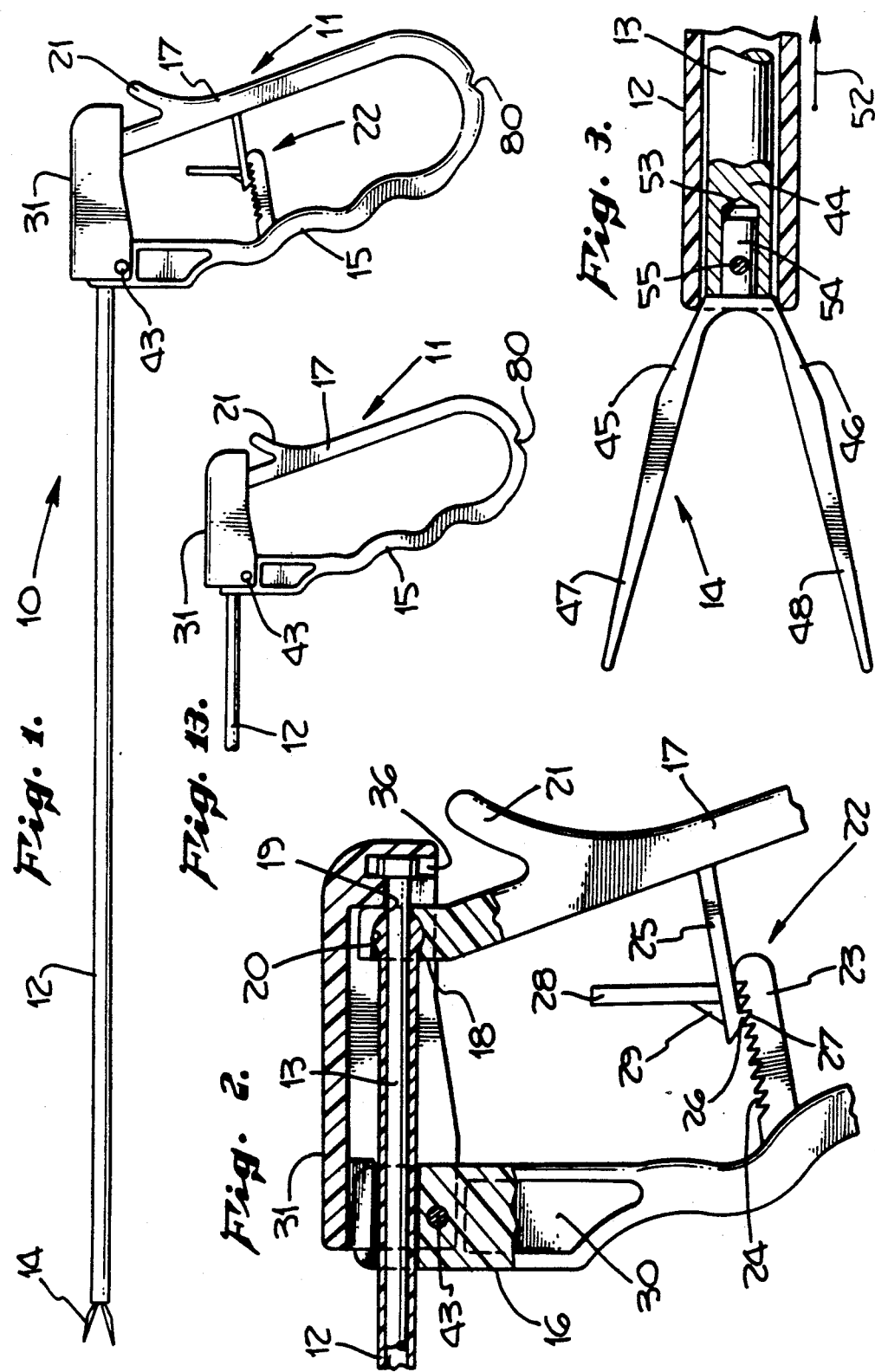

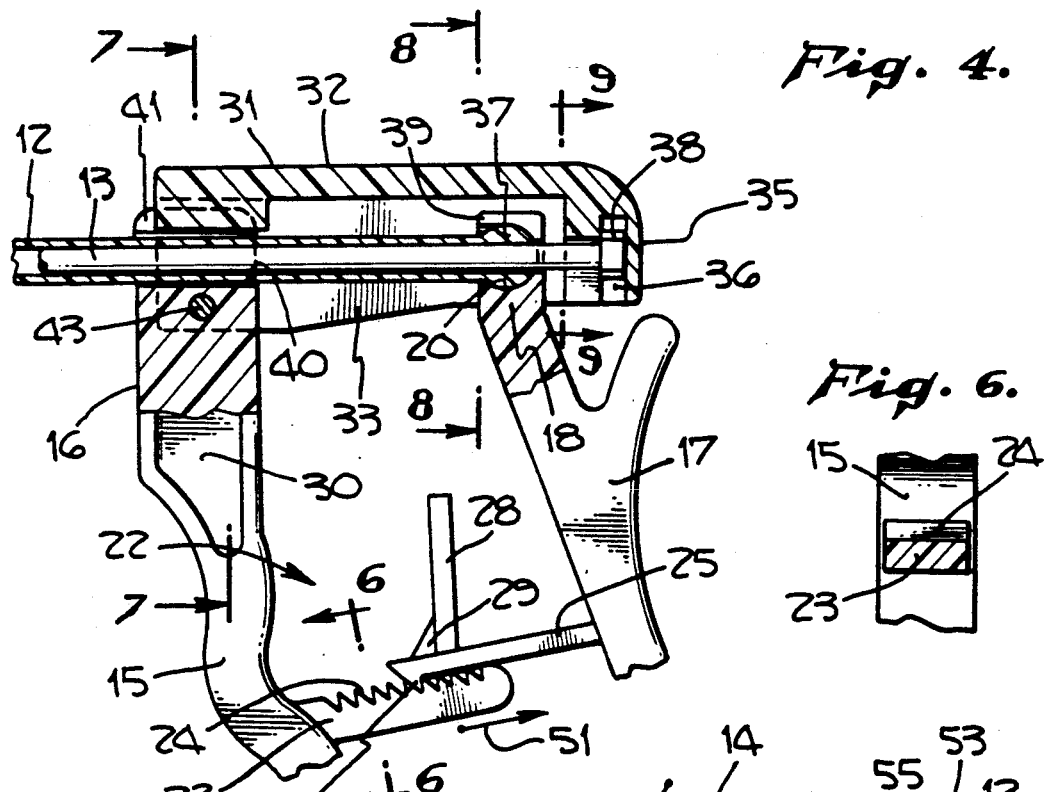

GRAPSING FORCEPS

BACKGROUND OF THE INVENTION

1. Field of the Invention

The invention relates to forceps; and, more particularly, to jaws fixed to a stylet mounted within a cannula for grasping tissue material between the jaws.

2. Description of the Prior Art

Forceps for grasping tissue material between the jaws thereof are well known in the art. However, such forceps have heretofore been unsuccessful in grasping and holding tissue material at a precise location in a controlled manner. For example, in German Patent No. 116823 to Haslinger, the jaws 1 must be withdrawn into cannula 3 in order to close and grasp tissue. Thus, when the surgeon is ready to grasp tissue using the Haslinger device, the surgeon must withdraw jaws 1 first which might disengage the jaws 1 from the tissue. Accordingly, no precise control is possible.

The device in U.S. Pat. No. 2,113,246 to Wappler, and in similar such forceps, was designed to overcome the problems of the Haslinger-type device. However, the Wappler device is quite complex requiring careful machining of parts. The wires or hinges of the Wappler device can break off leaving small foreign pieces inside of the patient. The rod 14 of Wappler is advanced to open and close the jaws 11. Thus, the precise position of the jaws inside of the patient can be thrown off.

There is thus a need for forceps which maintain the jaws stationary while simultaneously open and closing the same. This should be carried out in a quick and easy manner using fewer parts than complicated devices such as known in the prior art.

SUMMARY OF THE INVENTION

It is an object of this invention to provide grasping forceps having a stylet telescopingly mounted within a cannula having jaws at the end of the stylet which can be opened and closed without longitudinal movement of the stylet within the cannula.

It is a further object of this invention to having forceps as in the foregoing object wherein the stylet and cannula are mounted to a flexible handle.

It is still further an object of this invention to provide forceps as in the foregoing objects having a ratchet mechanism associated with the handle for precise control of the jaws.

It is a further object of this invention to provide a flexible handle for forceps as in the foregoing objects wherein the stylet is fixed to the handle at one end and extends through the cannula which is also both fixed to the handle at one end and slidable within a cavity in the handle.

These and other objects are preferably accomplished by providing forceps for grasping tissue material comprising a stationary stylet telescopingly disposed within a cannula. Jaws are mounted to one end of the stylet and the other end of the stylet is fixedly mounted in a handle. The cannula is mounted to the handle for sliding movement over the jaws to selectively compress and release the same to grasp and release tissue material or the like engaged by the jaws. Various types of jaws can be interchangeably mounted to the stylet.

BRIEF DESCRIPTION OF THE DRAWING

FIG. 1 is a vertical view of apparatus in accordance with the teachings of the invention;

FIG. 2 is a vertical view, partly in section, of a portion of the apparatus of FIG. 1;

FIG. 3 is a vertical view, partly in section, of another portion of the apparatus of FIG. 1;

FIG. 4 is a view similar to FIG. 2 illustrating another position of the parts thereof;

FIG. 5 is a view similar to FIG. 3 illustrating another position of the apparatus of FIG. 3;

FIGS. 6, 7, 8 and 9 are views taken along lines 6—6; 7—7; 8—8; and 9—9; respectively, of FIG. 4;

FIG. 13 is a vertical view of a portion of the apparatus of FIG. 1 illustrating a modification of the handle thereof.

DESCRIPTION OF THE PREFERRED EMBODIMENTS

Figure 10:
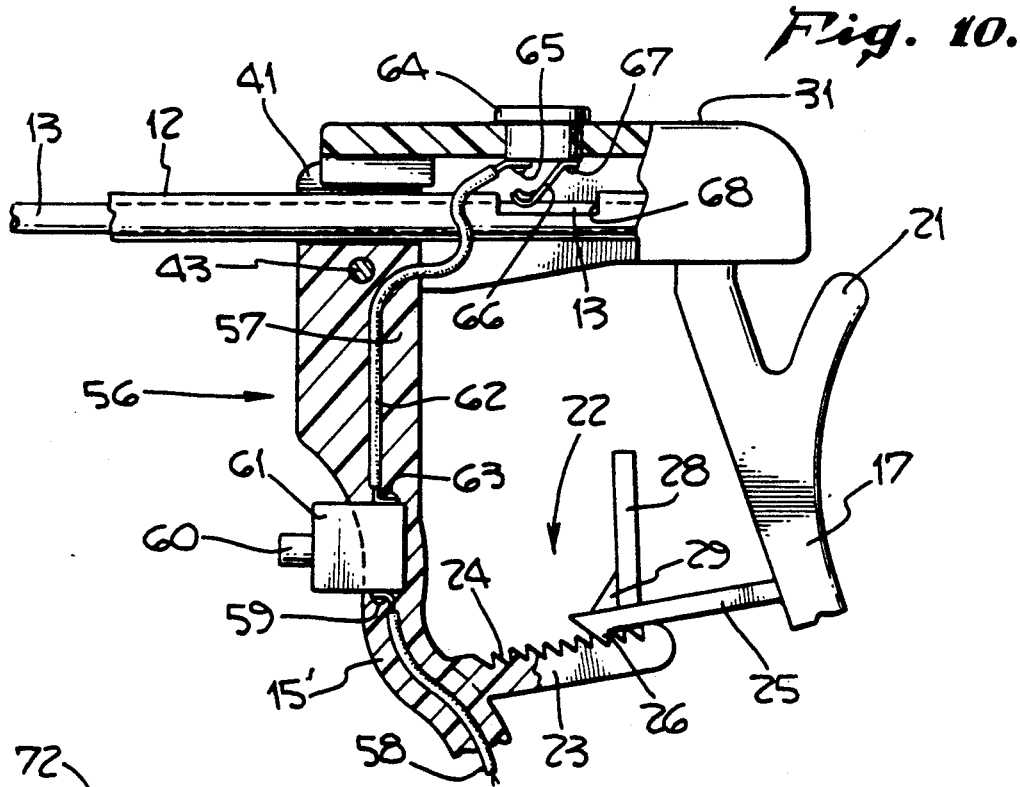
FIG. 10 is a view similar to FIG. 2 illustrating a modification thereof.

Referring now to FIG. 1 of the drawing, universal forceps apparatus 10 is shown comprised of a handle 11, a cannula 12 and a stylet 13 (see FIG. 2) terminating at the distal end thereof in jaws 14 (FIG. 1). Handle 11 is generally U-shaped in cross-section having a contoured frontal portion 15 for conforming to the fingers of the user. The width thereof is suitable for grasping by the user. As seen in FIGS. 1 and 2, handle 11 may be comprised of a single piece of molded plastic material, the frontal portion 15 being enlarged at enlarged portion 16 and the rear portion 17 terminating at the upper end in a terminal end 18 having a throughbore 19 with a forward facing circular cavity 20 communicating with throughbore 19. An extension portion 21 branches off at the upper end of rear portion 17 extending rearwardly, upwardly and outwardly as clearly seen in FIG. 2, to provide a thumb rest.

A linear ratchet mechanism 22 is provided between frontal and rear portions 15, 17 as seen in FIG. 2. A first ratchet member 23, having a plurality of spaced teeth 24 thereon, extends outwardly and linearly from frontal portion 15 (see also FIG. 6). Ratchet member 23 may be fixedly secured to frontal portion 15 and may be a separate part or an integral molded part thereof (see the embodiment of FIG. 10 showing another embodiment of the invention, the ratchet mechanism 22 being otherwise the same in both embodiments). An elongated tooth engaging member 25 extends from rear portion 17 and may also be an integral part thereof or a separate element fixedly secured thereto. Member 25 terminates at the end in a downwardly extending tooth 26 conforming to the spacing between teeth 24 and adapted to engage therebetween. Tooth 26 is angled or sloped, as at slope 27, at its leading edge so as to slide over teeth 24 (which may also be angled or sloped as shown). A finger engaging arm 28 extends upwardly from member 25 connected to or integral with member 25. A bracket 29 secured between arm 28 and member 25 braces arm 28.

A reduced thickness area 30 may be provided on both sides of enlarged portion 16 (FIG. 7) to reduce the overall weight of handle 11 and material comprising the same. As seen in FIG. 2, a cover 31 closes off the upper end of handle 11 which cover 31 is generally U-shaped (see FIGS. 7-9) having a top wall 32, and interconnected spaced side walls 33, 34. Cover 31 curves or extends downwardly at the rear (FIG. 4) forming an enlarged rear wall portion 35. A vertical slot 36, open at the bottom, is provided on rear wall portion 35. The rear end of stylet 13 terminates in an enlarged portion 38 fitting into slot 36. The rear end of cannula 12 terminates in a round knob 37 fitting into cavity 20. As seen in FIG. 8, the upper end of rear portion 17 of handle 11 has a slot 39 therein.

The upper end of enlarged portion 16 (FIG. 4) has a throughbore 40 (see also FIG. 7) open at the top with tapered walls 41, 42 leading thereto. Cover 31 is secured to the handle 11 by a pin 43 (see FIGS. 1, 2, 4 and 7) extending through side walls 33, 34 and enlarged portion 16.

The forward end 44 (FIG. 3) of stylet 13 has a generally round hole 53 therein receiving a round shaft 54 integral with or otherwise fixed to jaws 14. A pin 55 extends through shaft 54 and end 44 to retain jaws 14 to stylet 13. Of course, a removable screw or the like may be used in place of pin 55 to removably secure jaws 14 to stylet 13 so that the type of jaws or other gripping means may be quickly and easily changed.

Jaws 14 are preferably V-shaped as seen in FIG. 3.

In operation, handle 11 is gripped by the user and flexed due to its configuration and materials. Although ratchet mechanism 22 is preferred, such could be eliminated. This is shown in FIG. 13, as will be discussed further hereinbelow. However, in the embodiment of FIG. 1, member 25 slides over teeth 24 providing controlled flexing of the handle 11, with tooth 26 eventually locking into position between teeth 24 (FIG. 2) when a desired position of cannula 12 is reached.

In any event, such flexing moves cannula 12 back and forth over jaws 14. When cannula 12 moves over jaws 14, it presses thereagainst closing the same (FIG. 5). The jaws 14 are thus preferably configured to have outer sloped portions 45, 46 on each side thereof, rearwardly of integral clamping portions 47, 48, respectively, whereby cannula 12 can ride therealong forcing portions 47, 48 in the direction of arrows 49, 50 (FIG. 5) thereby positively closing the same. When arm 28 is lifted to disengage tooth 26 from teeth 24 and moved in the direction of arrow 51 (FIG. 4), cannula 12 is moved in the direction of arrow 52 (FIG. 3) to thereby allow cannula 12 to slide along sloped portions 45, 46 until jaws 14 are in the FIG. 3 position.

Enlarged portion 16 (FIG. 7) has throughbore 40 and tapered walls 41, 42 leading thereto providing a U-shaped channel through which cannula 12 slides when handle 11 is compressed. End 18 of rear portion 17 of handle 11 has a socket or cavity 20 wherein the terminal end or knob 38 of cannula 12 is fixed.

Cap 31 is fixed to the handle 11 by pin 43 at the front thereof and, at the rear, holds stylet 13 in place in slot 36.

Jaws 14 are preferably molded of a suitable plastic having a memory. However, other materials, such as spring stainless steel, may be used. The material used should have a memory and be useful in tissue grasping and/or holding.

It can be seen that there is disclosed apparatus 10 for squeezing handle 11 to close jaws 14. Jaws 14 are stationary at the point of grasping contact. Once contact is made with the tissue or other matter to be grasped by jaws 14, cannula 12 is driven forward over sloped portions 45, 46 to close jaws 14 and grasp the material (FIG. 5). Jaws 14 are doubled articulated for a more positive hold.

Although a particular embodiment has been disclosed in FIG. 10, this embodiment may be modified to provide the selective introduction of electric current through stylet 13 to jaws 14 for coagulation of bleeders. Thus, as seen in FIG. 10 wherein like numerals refer to like parts of the embodiment of FIGS. 1 to 9, apparatus 56 is shown having a handle 57 wherein front portion 15' is provided with an electrical conduit 58 extending therethrough (preferably molded therein) leading to a suitable power source (not shown). Conduit 58 is coupled, via connector 59, to a conventional push button assembly 61, operated by button 60, extending outwardly from handle front portion 15'. A second electrical conduit 62, connected via connector 63 to assembly 61, is also molded or otherwise extends through handle front portion 15' to a connector 65 of a terminal 64 mounted in cover 31 (or molded therein). An electrode 66, connected to terminal 64, via connector 67, extends downwardly therefrom through a slot or opening 68 in cannula 12 and in direct sliding contact with stylet 13 extending therethrough. Thus, actuating button 61 will selectively provide electrical current through stylet 13. In this embodiment, jaws 14 and stylet 13 must necessarily be of an electrically conductive material, such as spring stainless steel for stylet 13 and spring stainless steel for jaws 14.

Figure 11:
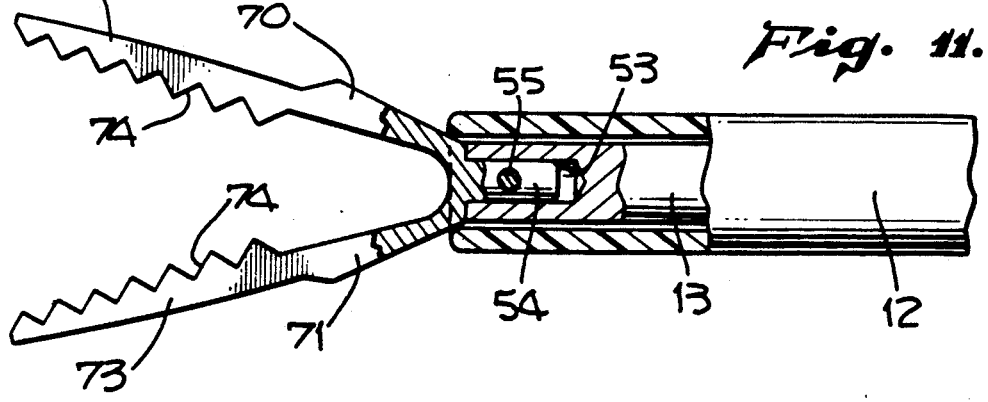
FIGS. 11 and 12 are views similar to FIG. 3 illustrating two modifications of the jaws of FIG. 3.
Figure 12:
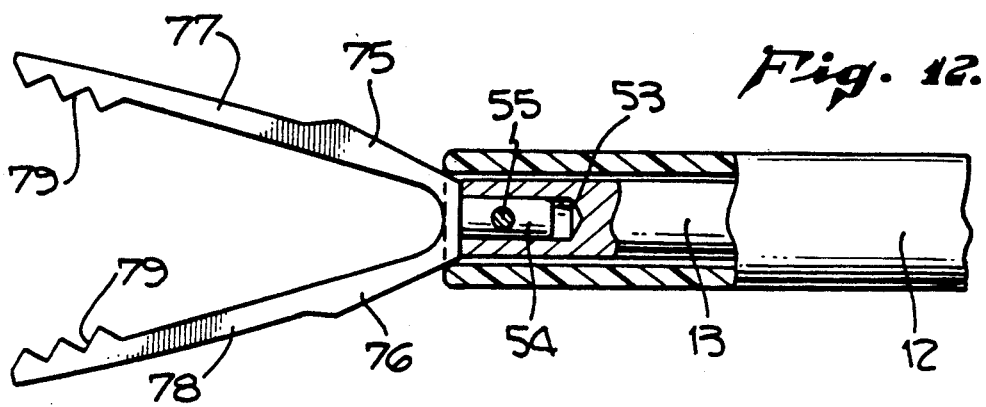

Although particularly configured jaws 14 are disclosed in the embodiments of FIGS. 1 to 10, obviously variations or modifications thereof may be used. Thus, as seen in FIGS. 11 and 12, wherein like numerals refer to like parts of the embodiment of FIGS. 1 to 9, jaws 69 (FIG. 11) may be a single piece of material, such as molded plastic or spring stainless steel, having sloped portions 70, 71 integral with elongated toothed portions 72, 73, respectively. Toothed portions 72, 73 each have a plurality of opposed teeth 74 for firmly and securely grasping material or the like therebetween. The apparatuses disclosed herein can be held and used in any orientation.

In the embodiment of FIG. 12, sloped portions 75, 76 are integrally connected to elongated toothed portions 77, 78, respectively, having opposed teeth 79 only adjacent the terminal ends thereof.

As discussed above, ratchet mechanism 22 may be eliminated. Thus, in FIG. 13, wherein like numerals refer to like parts of the embodiment of FIG. 1, ratchet mechanism 22 has been eliminated and handle 11 is flexed merely by selectively compressing and releasing frontal and rear portions 15, 17, notch 80 assisting in such flexing.

Differing jaws may be quickly and easily changed on the stylet 13 via pin 55. The jaws ride inside of cannula 12 and thus stay fixed allowing precise alignment and grasping of tissue. The teeth on the jaws may be of varying depths to provide for use in heavy tissue. If desired, a notch 80 (FIG. 1) may be provided at the bottom of handle 11 to facilitate flexing.

Any suitable materials may be used, such as the polymeric thermoplastic material manufactured and sold by General Electric under the trademark Ultem 1000. The jaws and cannula may be of this material.

I claim:

1. Apparatus for grasping human tissue or the like comprising:
   a flexible handle having a first portion spaced from a second portion and an elongated hollow cannula having one end fixed to said second portion and extending through said first portion and the other end opening externally of and remote from said handle;

an elongated stylet telescopingly and slidably mounted within said cannula having one end fixed to said handle and the other end terminating adjacent the open end of said cannula;

a pair of integrally connected resilient spaced gripping members coupled to the distal end of said stylet, each of said gripping members extending away from the distal end of said stylet and outwardly therefrom each other, said open end of said cannula being adapted to abut against said gripping members when said handle is squeezed, whereby said cannula moves linearly with respect to said handled while said stylet remains stationary and the open end of said cannula moves over said gripping members forcing them together to grasp human tissue therebetween; and a cover disposed on top of said first and second portions, said stylet being connected to said cover.

2. Apparatus for grasping human tissue or the like comprising:

a flexible handle having a first portion spaced from a second portion and an elongated hollow cannula having one end fixed to said second portion and extending through said first portion and the other end opening externally of and remote from said handle;

an elongated stylet telescopingly and slidably mounted within said cannula having one end fixed to said handle and the other end terminating adjacent the open end of said cannula; and a pair of integrally connected resilient spaced gripping members coupled to the distal end of said stylet, each of said gripping members extending away from the distal end of said stylet and outwardly therefrom each other, said open end of said cannula being adapted to abut against said gripping members when said handle is squeezed, whereby said cannula moves linearly with respect to said handle while said stylet remains stationary and the open end of said cannula moves over said gripping members forcing them together to grasp human tissue therebetween, said first portion including an open ended cavity therein, said cannula riding in said cavity, and a cover closing off said cavity and said second portion of said handle, said cover having a slot therein rearwardly of said second portion receiving said stylet therein in a fixed relationship.

3. Apparatus for grasping human tissue or the like comprising:

a flexible handle having a first portion spaced from a second portion and an elongated hollow cannula having one end fixed to said second portion and extending through said first portion and the other end opening externally of and remote from said handle;

an elongated stylet telescopingly and slidably mounted within said cannula having one end fixed to said handle and the other end terminating adjacent the open end of said cannula;

a pair of integrally connected resilient spaced gripping members coupled to the distal end of said stylet, each of said gripping members extending away from the distal end of said stylet and outwardly therefrom each other, said open end of said cannula being adapted to abut against said gripping members when said handle is squeezed, whereby said cannula moves linearly with respect to said handle while said stylet remains stationary and the open end of said cannula moves over said gripping members forcing them together to grasp human tissue therebetween; and a cover closing off said first and second portions having a portion thereof disposed against said second portion, said stylet being connected to said portion of said cover, said cover being connected only to said first portion.

* * * * *